United States Patent [19]

Yoshizawa et al.

[11] Patent Number: 4,668,799

[45] Date of Patent: May 26, 1987

[54] ANTI-HEPATITIS AND ANTI-CIRRHOTIC 1,3-DITHIOL-2-YLIDENE DERIVATIVES, AND PHARMACEUTICAL COMPOSITIONS THEREFOR

[75] Inventors: Junji Yoshizawa, Machida; Yoshimi Tsuchiya, Funabashi; Yukio Hirayama, Yokohama; Kaoru Shimada, Gifu; Nobuyuki Mino, Ichikawa; Kyoko Nakamichi; Ikuo Matsumoto, both of Tokyo, all of Japan

[73] Assignee: Banyu Pharmaceutical Co., Ltd., Tokyo, Japan

[21] Appl. No.: 739,182

[22] Filed: May 30, 1985

[51] Int. Cl.[4] .............. A61K 31/385; A61K 31/415; A61K 31/44; A61K 31/495; C07D 339/06; C07D 401/02; C07D 403/04; C07D 409/04

[52] U.S. Cl. ................... 514/252; 514/253; 514/312; 514/313; 514/314; 514/336; 514/337; 514/338; 514/341; 514/343; 514/394; 514/395; 514/397; 514/414; 514/422; 514/436; 544/238; 546/155; 546/156; 546/168; 546/271; 546/273; 546/278; 546/284; 548/327; 548/336; 548/455; 548/460; 548/468; 548/520; 548/527; 549/39

[58] Field of Search ............... 544/238; 546/155, 156, 546/168, 271, 273, 278, 284; 548/327, 336, 455, 460, 468, 520, 527; 549/39; 514/252, 253, 312, 313, 314, 336, 337, 338, 341, 343, 394, 395, 397, 414, 422, 436

[56] References Cited

U.S. PATENT DOCUMENTS 4,035,387  7/1977  Taninaka et al. ............ 549/39
4,118,506 10/1978  Taninaka et al. ............ 549/39

FOREIGN PATENT DOCUMENTS 49-35272  9/1974  Japan ............................ 549/39

OTHER PUBLICATIONS

Nihon, Abstract 84-097445/16 of J.P. 150705 3/8/84.
Hirai et al, CA vol. 83, 1975, 83:10035t, p. 843.
Yoshizawa et al, CA vol. 104, 1986, 104:109609x, p. 725.
Yoshizawa et al, CA vol. 104, 1986, 104:109613u, p. 725-726.
Hirai et al, Certified Translation for JP 4935272 Nov. 20, 1986.

Primary Examiner—John M. Ford
Assistant Examiner—J. G. Mullins
Attorney, Agent, or Firm—Oblon, Fisher, Spivak, McClelland & Maier

[57] ABSTRACT

A 1,3-dithiol-2-ylidene derivative of the formula:

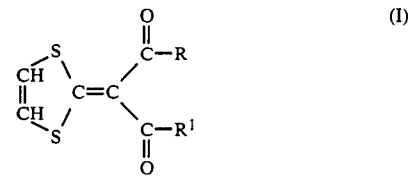

wherein each of R and $R^1$ which may be the same or different, is a lower alkyl group, a lower alkenyl group, a cycloalkyl group, a lower alkoxyalkyl group, or a substituted or unsubstituted aryl, aralkyl or heterocyclic group, or R and $R^1$ together form a substituted or unsubstituted ethylene or trimethylene group.

6 Claims, No Drawings

ANTI-HEPATITIS AND ANTI-CIRRHOTIC 1,3-DITHIOL-2-YLIDENE DERIVATIVES, AND PHARMACEUTICAL COMPOSITIONS THEREFOR

The present invention relates to novel 1,3-dithiol derivatives, a process for their production and a pharmaceutical composition for treating the liver diseases.

It is known that there are a large number of patients who suffer from liver damages caused by various factors such as alcohol, malnutrition, viruses, chemicals, toxicants, etc. The liver diseases may generally be classified by their types into acute hepatitis, chronic hepatitis, liver cirrhosis, and fulminant hepatitis. It is said to be very difficult to treat these liver diseases. Namely, currently available methods for the treatment such as treatments with pharmaceuticals e.g. liver protective agents such as various vitamins, saccharides, amino acids, glutathione, glycyrrhizin, liver hydrolyzates or adrenocortical hormones; cholagogues; immunomodulaters; or antiviral substances against viral hepatitis, are all nothing more than symptomatic treatments, and they are not adequately effective for the treatment of the existing liver damages.

It has recently been reported that 1,3-dithiol derivatives represented by Malotilate as identified below, are effective for the treatment of liver damages (see Japanese Examined Patent Publications No. 18,576/1981, No. 18,577/1981 and No. 18,578/1981).

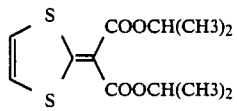

Malotilate

As a result of extensive researches, the present inventors have found that certain novel 1,3-dithiol derivatives represented by the after-mentioned formula I, exhibit excellent activities for the treatment of a wide spectrum of liver damages, which are comparable or superior to the above-mentioned conventional 1,3-dithiol derivatives. The present invention has been accomplished on the basis of this discovery.

Namely, the present invention provides a 1,3-dithiol-2-ylidene derivative of the formula:

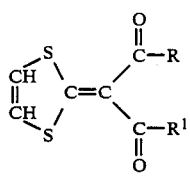

wherein each of R and $R^1$ which may be the same or different, is a lower alkyl group, a lower alkenyl group, a cycloalkyl group, a lower alkoxyalkyl group, or a substituted or unsubstituted aryl, aralkyl or heterocyclic group or R and $R^1$ together form a substituted or unsubstituted ethylene or trimethylene group.

The compounds of the formula (I) of the present invention are effective for stimmulating, improving and recovering the liver functions, and are useful as preventive and curative drugs for various liver troubles.

The present invention also provides a process for producing the compound of the formula I, which comprises reacting a β-diketone of the formula:

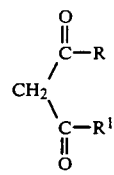

wherein R and $R^1$ are as defined above, if necessary, protected by a suitable protective group, with a dithiolylium salt of the formula:

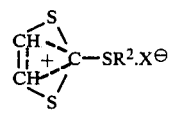

wherein $R^2$ is a lower alkyl group or an aralkyl group, and X is an anion residue, in the presence of a base, and, if necessary, removing the protective group.

Further, the present invention provides a pharmaceutical composition for treating the liver disease, which comprises an effective amount of the compound of the formula I and a pharmaceutically acceptable carrier or diluent.

Now, the present invention will be described in detail with reference to the preferred embodiments.

Referring to the definitions of R and $R^1$ in the formula I, the lower alkyl group includes methyl, ethyl, propyl, isopropyl, butyl, isobutyl, tert-butyl, pentyl and hexyl; the lower alkenyl group includes vinyl or 2-methylvinyl; the cycloalkyl group includes cyclopentyl and cyclohexyl; the lower alkoxyalkyl group includes ethoxymethyl, 2-methoxyethyl, 3-ethoxypropyl, 3-propoxypropyl and 2-ethoxybutyl; and the substituted or unsubstituted aryl, aralkyl or heterocyclic group includes a phenyl, naphthyl, benzyl, naphthylmethyl, furyl, thienyl, pyrrolyl, imidazolyl, pyridyl, pyrazinyl, indolyl, quinolyl or benzimidazolyl group which may be substituted by e.g. halogen, hydroxyl, lower alkyl, lower alkoxy, nitro, cyano or lower alkoxy carbonyl.

Further, R and $R^1$ may together form an ethylene or trimethylene group which may be substituted by e.g. a lower alkyl group, an aralkyl group and an aryl group. Here, the ower alkyl group includes methyl, ethyl, propyl, isopropyl, butyl, isobutyl, tert-butyl, pentyl and hexyl; the aralkyl group includes benzyl and naphthylmethyl; and the aryl group includes phenyl and naphthyl.

Specific examples of the compounds of the present invention may be mentioned as follows:

(1) 3-(1,3-dithiol-2-ylidene)-2,4-pentanedione (Compound 1)
(2) 3-(1,3-dithiol-2-ylidene)-2,4-hexanedione (Compound 2)
(3) 3-(1,3-dithiol-2-ylidene)-1-ethoxy-2,4-pentanedione (Compound 3)
(4) 5-(1,3-dithiol-2-ylidene)-2,8-dimethyl-4,6-nonanedione (Compound 4)
(5) 2-(1,3-dithiol-2-ylidene)-1-cyclohexyl-1,3-butanedione (Compound 5)
(6) 2-(1,3-dithiol-2-ylidene)-1-phenyl-1,3-butanedione (Compound 6)

(7) 2-(1,3-dithiol-2-ylidene)-1-phenyl-1,3-hexanedione (Compound 7)
(8) 2-(1,3-dithiol-2-ylidene)-5-methyl-1-phenyl-1,3-hexanedione (Compound 8)
(9) 2-(1,3-dithiol-2-ylidene)-4,4-dimethyl-1-phenyl-1,3-pentanedione (Compound 9)
(10) 2-(1,3-dithiol-2-ylidene)-1-phenyl-1,3-octadecanedione (Compound 10)
(11) 2-(1,3-dithiol-2-ylidene)-1-phenyl-4-hexene-1,3-dione (Compound 11)
(12) 2-(1,3-dithiol-2-ylidene)-1-(4-methylphenyl)-1,3-butanedione (Compound 12)
(13) 2-(1,3-dithiol-2-ylidene)-1-(4-fluorophenyl)-1,3-butanedione (Compound 13)
(14) 2-(1,3-dithiol-2-ylidene)-1-(4-chlorophenyl)-1,3-butanedione (Compound 14)
(15) 2-(1,3-dithiol-2-ylidene)-1-(4-bromophenyl)-1,3-butanedione (Compound 15)
(16) 2-(1,3-dithiol-2-ylidene)-1-(2-methoxyphenyl)-1,3-butanedione (Compound 16)
(17) 2-(1,3-dithiol-2-ylidene)-1-(4-methoxyphenyl)-1,3-butanedione (Compound 17)
(18) 2-(1,3-dithiol-2-ylidene)-1-(3,4-dimethoxyphenyl)-1,3-butanedione (Compound 18)
(19) 2-(1,3-dithiol-2-ylidene)-1-(4-nitrophenyl)-1,3-butanedione (Compound 19)
(20) 2-(1,3-dithiol-2-ylidene)-1-(2-pyridyl)-1,3-butanedione (Compound 20)
(21) 2-(1,3-dithiol-2-ylidene)-1-(3-pyridyl)-1,3-butanedione (Compound 21)
(22) 2-(1,3-dithiol-2-ylidene)-1-(4-pyridyl)-1,3-butanedione (Compound 22)
(23) 2-(1,3-dithiol-2-ylidene)-1-(2-furyl)-1,3-butanedione (Compound 23)
(24) 2-(1,3-dithiol-2-ylidene)-1-(2-thienyl)-1,3-butanedione (Compound 24)
(25) 2-(1,3-dithiol-2-ylidene)-1-(2-pyrrolyl)-1,3-butanedione (Compound 25)
(26) 2-(1,3-dithiol-2-ylidene)-1-pyrazinyl-1,3-butanedione (Compound 26)
(27) 2-(1,3-dithiol-2-ylidene)-1-(1-naphthyl)-1,3-butanedione (Compound 27)
(28) 2-(1,3-dithiol-2-ylidene)-1-(2-naphthyl)-1,3-butanedione (Compound 28)
(29) 2-(1,3-dithiol-2-ylidene)-1-(2-indolyl)-1,3-butanedione (Compound 29)
(30) 2-(1,3-dithiol-2-ylidene)-1-(2-quinolyl)-1,3-butanedione (Compound 30)
(31) 2-(1,3-dithiol-2-ylidene)-1-phenyl-4,4,4-trifluoro-1,3-butanedione (Compound 31)
(32) 3-(1,3-dithiol-2-ylidene)-1-phenyl-2,4-pentanedione (Compound 32)
(33) 4-(1,3-dithiol-2-ylidene)-1-phenyl-1-hexene-3,5-dione (Compound 33)
(34) 2-(1,3-dithiol-2-ylidene)-1,3-diphenyl-1,3-propanedione (Compound 34)
(35) 2-(1,3-dithiol-2-ylidene)-1,3-di(4-chlorophenyl)-1,3-propanedione (Compound 35)
(36) 2-(1,3-dithiol-2-ylidene)-1,3-di(4-methoxyphenyl)-1,3-propanedione (Compound 36)
(37) 2-(1,3-dithiol-2-ylidene)-1,4-diphenyl-1,3-butanedione (Compound 37)
(38) 4-(1,3-dithiol-2-ylidene)-1,5-diphenyl-1-pentene-3,5-dione (Compound 38)
(39) 4-(1,3-dithiol-2-ylidene)-1,7-diphenyl-1,6-heptadiene-3,5-dione (Compound 39)
(40) 2-(1,3-dithiol-2-ylidene)-1,3-cyclopentanedione (Compound 40)
(41) 2-(1,3-dithiol-2-ylidene)-1,3-cyclohexanedione (Compound 41)
(42) 2-(1,3-dithiol-2-ylidene)-4-methyl-1,3-cyclohexanedione (Compound 42)
(43) 2-(1,3-dithiol-2-ylidene)-4-(2-methylethyl)-1,3-cyclohexanedione (Compound 43)
(44) 2-(1,3-dithiol-2-ylidene)-5,5-dimethyl-1,3-cyclohexanedione (Compound 44)
(45) 3-(1,3-dithiol-2-ylidene)-1-(4-hydroxylphenyl)-1,3-butanedione (Compound 45)
(46) 2-(1,3-dithiol-2-ylidene)-1-(4-aminophenyl)-1,3-butanedione (Compound 46)
(47) 2-(1,3-dithiol-2-ylidene)-1-(2-benzimidazolyl)-1,3-butanedione (Compound 47)

However, the present invention is not restricted to these specific examples.

According to the present invention, the compound of the formula I can be prepared by reacting the β-diketone of the formula II, if necessary, protected by a suitable protective group, with the dithiolium salt of the formula III in the presence of a base, and, if necessary, removing the protective group.

As the β-diketone of the formula II, there may be mentioned, for instance, 2,4-pentanedione, 2,4-hexanedione, 1-ethoxy-2,4-pentanedione, 2,8-dimethyl-4,6-nonanedione, 1-cyclohexyl-1,3-butanedione, 1-phenyl-1,3-butanedione, 1-phenyl-1,3-hexanedione, 5-methyl-1-phenyl-1,3-hexanedione, 4,4-dimethyl-1-phenyl-1,3-pentanedione, 1-phenyl-1,3-octadecanedione, 1-phenyl-4-hexene-1,3-dione, 1-(4-methylphenyl)-1,3-butanedione, 1-(4-fluorophenyl)-1,3-butanedione, 1-(4-chlorophenyl)-1,3-butanedione, 1-(4-bromophenyl)-1,3-butanedione, 1-(2-methoxyphenyl)-1,3-butanedione, 1-(4-methoxyphenyl)-1,3-butanedione, 1-(3,4-methoxyphenyl)-1,3-butanedione, 1-(4-nitrophenyl)-1,3-butanedione, 1-(2-pyridyl)-1,3-butanedione, 1-(3-pyridyl)-1,3-butanedione, 1-(4-pyridyl)-1,3-butanedione, 1-(2-furyl)-1,3-butanedione, 1-(2-thienyl)-1,3-butanedione, 1-(2-pyrrolyl)-1,3-butanedione, 1-pyrazinyl-1,3-butanedione, 1-(1-naphthyl)-1,3-butanedione, 1-(2-naphthyl)-1,3-butanedione, 1-(2-indolyl)-1,3-butanedione, 1-(2-quinolyl)-1,3-butanedione, 1-phenyl-4,4,4-trifluoro-1,3-butandedione, 1-phenyl-2,4-pentanedione, 1-phenyl-1-hexene-3,5-dione, 1,3-diphenyl-1,3-propanedione, 1,3-di(4-chlorophenyl)-1,3-propanedione, 1,3-di(4-methoxyphenyl)-1,3-propanedione, 1,4-diphenyl-1,3-butanedione, 1,5-diphenyl-1-pentene-3,5-dione, 1,7-diphenyl-1,6-heptadiene-3,5-dione, 1,3-cyclopentanedione, 1,3-cyclohexanedione, 4-methyl-1,3-cyclohexanedione, 4-(2-methylethyl)-1,3-cyclohexanedione, 5,5-dimethyl-1,3-cyclohexanedione, 1-(4-methoxymethyloxyphenyl)-1,3-butanededione, 1-(4-t-butoxycarbonylaminophenyl)-1,3-butanedione, and 1-(2-benzimidazolyl)-1,3-butanedione.

Such β-diketones of the formula II may be available as commercial products, or may otherwise readily be prepared by one of the following two methods:

Method A

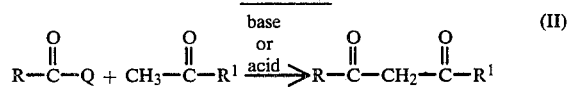
(II)

Method B

-continued

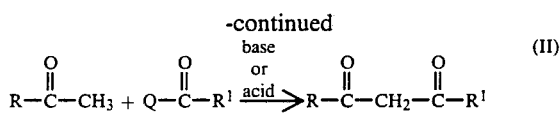
(II)

IN the above formulas, R and R¹ are as defined above, and Q is an active group of a carboxyl group.

The protective group for the β-diketone may be of any type so long as it does not adversely affect the product when it is removed from the product. As specific examples of the protective group, there may be mentioned a tert-butoxycarbonyl group, a benzyloxycarbonyl group, a benzyl group, and a methoxymethyl group.

The dithiolylium salt of the formula III may be synthesized by alkylating 1,3-dithiol-2-thione by means of e.g. methyl iodide, ethyl iodide or dimethyl sulfate, or benzylating it with e.g. benzyl chloride.

In carrying out the process of the present invention, the reaction of the β-diketone of the formula II with the dithiolylium salt of the formula III in the presence of a base is preferably conducted by using a suitable solvent. As such a solvent, it is desirable to use a solvent inert to the reaction. For instance, there may be mentioned tetrahydrofuran, dioxane, methanol, acetic acid, dimethyl sulfoxide and dimethylformamide. These solvents may be used alone or in combination as a mixture.

The molar ratios of the dithiolylium salt and the base relative to the β-diketone are not critical. However, it is preferred to use the stoichiometric amount of dithiolylium salt and the stoichiometric amount or an excess amount of the base relative to the β-diketone. The reaction is conducted usually within a temperature range of from 0° C. to the boiling point of the solvent. However, the reaction may be conducted at a temperature lower or higher than this range in order to control the reaction rate.

As the base to be used in the present invention, there may be mentioned inorganic bases such as metal sodium, sodium hydride, sodium methoxide, sodium hydroxide, potassium hydroxide, sodium carbonate and potassium carbonate, and organic bases such as pyridine, triethylamine and dimethylaniline.

The reaction produces no substantial by-products. Therefore, after-treatment of the reaction is very simple. Namely, after the completion of the reaction, the desired product is extracted from the reaction mixture with a suitable solvent, followed by the removal of the solvent, whereby the desired product is obtained. If necessary, the desired product can be separated and purified by recrystallization or by column chromatography.

When the compound of the present invention is to be used as a drug for treating the liver disease, its dose is usually from 0.1 to 25 mg a day per kg of the body weight in the case of oral administration, and from 0.01 to 10.0 mg a day per kg of the body weight in the case of parenteral administration, although it may vary depending upon the body weight, age, sex or health condition of the patient, the manner of administration or the degree of disease.

The compound of the present invention may be formulated into various forms such as tablets, granules, powders, suspensions, capsules, solutions for injection or isotonic solutions in accordance with the conventional methods which are commonly used in the technical fields for pharmaceutical formulations.

For the production of solid formulations for oral administration, the active ingredient is incorporated with a vehicle and necessary additives such as a condensing agent, a disintegrator, a lubricant, a coloring agent, or a taste- or odor-controlling agent, and then the mixture is formed into tablets, coated tablets, granules, powders or capsules by conventional methods.

For the preparation of injection solutions, the active ingredient is incorporated with a pH controlling agent, a buffer, a suspending agent, a dissolving agent, a stabilizer, an isotonic agent, a storage assistant, etc., if required, and the mixture is formulated into hypodermic, intramuscular or intravenous injection solutions by conventional methods.

Now, the present invention will be described in further detail with reference to Examples. However, it should be understood that the present invention is by no means restricted to these specific Examples.

EXAMPLE 1

To 20 ml of dry tetrahydrofuran, 0.5 g of 50% oil-based sodium hydride was suspended, and 1.0 g of 2,4-pentanedione was gradually added under cooling with ice. After the completion of the generation of hydrogen gas, 2.5 g of 2-methylthio-1,3-dithiolylium perchlorate was added thereto, and the mixture was stirred at room temperature for three hours. Then, the solvent was removed from the reaction solution by distillation under reduced pressure. Ice water was added to the residue, and then the desired product was extracted with chloroform. The chloroform extract was concentrated under reduced pressure, and the residue was recrystallized from benzene, whereby 1.8 g (yield: 90%) of 3-(1,3-dithiol-2-ylidene)-2,4-pentanedione (Compound 1) was obtained as crystals having a melting point of from 159° to 160° C.

IR $\nu_{max}^{KBr}$ cm$^{-1}$: 3010, 1570, 1370, 1320, 1270.

NMR (CDCl$_3$) δ: 7.4 (2H, s), 2.6 (6H, s).

EXAMPLES 2–44

In the same manner as in Example 1, the following compounds were obtained.

EXAMPLE 2

3-(1,3-dithiol-2-ylidene)-2,4-hexanedione (Compound 2)

mp.: 90° C. (recrystallized from n-hexane).

IR $\nu_{max}^{KBr}$ cm$^{-1}$: 3000, 1570, 1365, 1320, 1270.

NMR (CDCl$_3$) δ: 7.3 (2H, s), 2.8 (2H, q), 2.6 (3H, s), 1.2 (3H, t).

EXAMPLE 3

3-(1,3-dithiol-2-ylidene)-1-ethoxy-2,4-pentanedione (Compound 3)

mp.: 85° C. (recrystallized from benzene-n-hexane).

IR $\nu_{max}^{KBr}$ cm$^{-1}$: 3020, 1580, 1380, 1320, 1280.

NMR (CDCl$_3$) δ: 7.4 (2H, s), 4.6 (2H, s), 3.6 (2H, q), 2.7 (2H, s), 1.3 (3H, t).

EXAMPLE 4

5-(1,3-dithiol-2-ylidene)-2,8-dimethyl-4,6-nonanedione (Compound 4)

mp.: 75°–76° C. (recrystallized from benzene-n-hexane).

IR $\nu_{max}^{KBr}$ cm$^{-1}$: 3010, 1580, 1480, 1340, 1320.

NMR (CDCl$_3$) δ: 7.2 (2H, s), 2.7 (4H, d), 2.3 (2H, m), 0.9 (6H, d).

EXAMPLE 5

2-(1,3-dithiol-2-ylidene)-1-cyclohexyl-1,3-butanedione (Compound 5)

mp.: 104°–105° C. (recrystallized from methanol).
IR $\nu_{max}^{KBr}$ cm$^{-1}$: 2920, 1564, 1379, 1302.
NMR (CDCl$_3$) δ: 7.5 (2H, s), 2.7 (3H, s), 2.1–1.3 (5H, m).

EXAMPLE 6

2-(1,3-dithiol-2-ylidene)-1-phenyl-1,3-butanedione (Compound 6)

mp.: 108°–109° C. (recrystallized from ethyl acetate-benzene).
IR $\nu_{max}^{KBr}$ cm$^{-1}$: 3050, 1590, 1570, 1365, 1278
NMR (CDCl$_3$) δ: 7.5 (5H, m), 7.3 (2H, s), 1.9 (3H, s).

EXAMPLE 7

2-(1,3-dithiol-2-ylidene)-1-phenyl-1,3-hexanedione (Compound 7)

mp.: 65° C. (recrystallized from benzene-n-hexane).
IR $\nu_{max}^{KBr}$ cm$^{-1}$: 3070, 1570, 1450, 1370, 1340, 1280.
NMR (CDCl$_3$) δ: 7.5 (5H, m), 7.3 (2H, s), 2.2 (2H, t) 1.5 (2H, m), 0.7 (3H, t).

EXAMPLE 8

2-(1,3-dithiol-2-ylidene)-5-methyl-1-phenyl-1,3-hexanedione (Compound 8)

mp.: 63.5° C. (recrystallized from benzene-n-hexane).
IR $\nu_{max}^{KBr}$ cm$^{-1}$: 1620, 1580, 1570, 1380, 1362.
NMR (CDCl$_3$) δ: 7.5 (5H, m), 7.3 (2H, s), 2.0 (2H, d) 1.9 (1H, m), 0.7 (6H, d).

EXAMPLE 9

2-(1,3-dithiol-2-ylidene)-4,4-dimethyl-1-phenyl-1,3-pentanedione (Compound 9)

mp.: 91°–92° C. (recrystallized from chloroform-n-hexane).
IR $\nu_{max}^{KBr}$ cm$^{-1}$: 2900, 1630, 1580, 1560, 1382.
NMR (CDCl$_3$) δ: 7.3–7.8 (5H, m), 6.9 (2H, s), 1.0 (9H, s).

EXAMPLE 10

2-(1,3-dithiol-2-ylidene)-1-phenyl-1,3-octadecanedione (Compound 10)

mp.: 49°–50° C. (recrystallized from chloroform-n-hexane).
IR $\nu_{max}^{KBr}$ cm$^{-1}$: 2920, 2850, 1615, 1560, 1338, 708.
NMR (CDCl$_3$) δ: 7.3–7.7 (5H, m), 7.25 (2H, s), 2.2 (2H, t) 0.7–1.7 (29H, m).

EXAMPLE 11

2-(1,3-dithiol-2-ylidene)-1-phenyl-4-hexene-1,3-dione (Compound 11)

mp.: 83°–84.5° C. (recrystallized from ethyl ether-n-hexane).
IR $\nu_{max}^{KBr}$ cm$^{-1}$: 2910, 1640, 1600 1565, 1363.
NMR (CDCl$_3$) δ: 7.3–7.75 (5H, m), 7.3 (2H, s), 6.4–6.9 (1H, m), 5.75 (1H, d.q), 1.51 (3H, d.d).

EXAMPLE 12

2-(1,3-dithiol-2-ylidene)-1-(4-methylphenyl)-1,3-butanedione (Compound 12)

mp.: 161°–163° C. (recrystallized from acetone-n-hexane).
IR $\nu_{max}^{KBr}$ cm$^{-1}$: 3080, 1610, 1560, 1340, 1278.
NMR (CDCl$_3$) δ: 7.45 (2H, d), 7.2 (2H, s), 7.1 (2H, d) 2.35 (3H, s), 1.9 (3H, s).

EXAMPLE 13

2-(1,3-dithiol-2-ylidene)-1-(4-fluorophenyl)-1,3-butanedione (Compound 13)

mp.: 151°–152° C. (recrystallized from methanol).
IR $\nu_{max}^{KBr}$ cm$^{-1}$: 3050, 1600, 1560, 1350, 1275, 1230.
NMR (CDCl$_3$) δ: 7.7 (2H, d), 7.3 (2H, s), 7.2 (2H, d) 1.95 (3H, s).

EXAMPLE 14

2-(1,3-dithiol-2-ylidene)-1-(4-chlorophenyl)-1,3-butanedione (Compound 14)

mp.: 151°–152° C. (recrystallized from acetone-n-hexane).
IR $\nu_{max}^{KBr}$ cm$^{-1}$: 3080, 1580, 1370, 1322.
NMR (CDCl$_3$) δ: 7.75 (2H, d), 7.35 (2H, s), 7.21 (2H, d) 1.95 (3H, s).

EXAMPLE 15

2-(1,3-dithiol-2-ylidene)-1-(4-bromophenyl)-1,3-butanedione (Compound 15)

mp.: 137°–138° C. (recrystallized from benzene-n-hexane).
IR $\nu_{max}^{KBr}$ cm$^{-1}$: 3050, 1605, 1570, 1360, 1270, 1170.
NMR (CDCl$_3$) δ: 7.8 (2H, d), 7.5 (2H, s), 7.35 (2H, d) 1.9 (3H, s).

EXAMPLE 16

2-(1,3-dithiol-2-ylidene)-1-(2-methoxyphenyl)-1,3-butanedione (Compound 16)

mp.: 140.5° C. (recrystallized from acetone-petroleum ether).
IR $\nu_{max}^{KBr}$ cm$^{-1}$: 3000, 1592, 1560, 1340, 1308.
NMR (CDCl$_3$) δ: 6.6–7.5 (6H, m), 3.7 (3H, s), 1.9 (3H, s).

EXAMPLE 17

2-(1,3-dithiol-2-ylidene)-1-(4-methoxyphenyl)-1,3-butanedione (Compound 17)

mp.: 146° C. (recrystallized from methanol).
IR $\nu_{max}^{KBr}$ cm$^{-1}$: 3080, 1590, 1375, 1260, 1180.
NMR (CDCl$_3$) δ: 7.5 (2H, d), 7.1 (2H, s), 6.9 (2H, d), 3.7 (3H, s), 1.9 (3H, s).

EXAMPLE 18

2-(1,3-dithiol-2-ylidene)-1-(3,4-dimethoxyphenyl)-1,3-butanedione (Compound 18)

mp.: 192°–193° C. (recrystallized from ethanol)
IR $\nu_{max}^{KBr}$ cm$^{-1}$: 3000, 1605, 1560, 1420, 1350, 1270.
NMR (CDCl$_3$) δ: 7.15–7.35 (7H, m), 7.2 (2H, s), 6.85 (1H, d), 3.9 (6H, s), 2.0 (3H, s).

EXAMPLE 19

2-(1,3-dithiol-2-ylidene)-1-(4-nitrophenyl)-1,3-butanedione (Compound 19)

mp.: 151°–153° C. (recrystallized from benzene-hexane).

IR $\nu_{max}^{KBr}$ cm$^{-1}$: 3005, 1600, 1550, 1510, 1330, 1310 1280.

NMR (CDCl$_3$) δ: 8.25 (2H, d), 7.75 (2H, d), 7.4 (2H, s), 1.8 (3H, s).

EXAMPLE 20

2-(1,3-dithiol-2-ylidene)-1-(2-pyridyl)-1,3-butanedione (Compound 20)

mp.: 148°–149° C. (recrystallized from benzene).

IR $\nu_{max}^{KBr}$ cm$^{-1}$: 3050, 1620, 1570, 1370, 1330, 1265 1000.

NMR (CDCl$_3$) δ: 8.6 (1H, d.d), 7.9 (1H, d.d), 7.35 (1H, m), 7.35 (2H, s), 1.85 (3H, S).

EXAMPLE 21

2-(1,3-dithiol-2-ylidene)-1-(3-pyridyl)-1,3-butanedione (Compound 21)

mp.: 124°–125° C. (recrystallized from benzene-n-hexane).

IR $\nu_{max}^{KBr}$ cm$^{-1}$: 1610, 1580, 1420, 1350, 1300.

NMR (CDCl$_3$) δ: 8.7 (2H, q), 8.0 (1H, m), 7.4 (2H, s), 7.3 (1H, d), 2.0 (3H, s).

EXAMPLE 22

2-(1,3-dithiol-2-ylidene)-1-(4-pyridyl)-1,3-butanedione (Compound 22)

mp.: 146°–146.5° C. (recrystallized from ethyl acetate-petroleum ether).

IR $\nu_{max}^{KBr}$ cm$^{-1}$: 3030, 1560, 1540, 1400, 1342, 1270.

NMR (CDCl$_3$) δ: 8.7 (2H, d), 7.4 (2H, s), 7.35 (2H, d).

EXAMPLE 23

2-(1,3-dithiol-2-ylidene)-1-(2-furyl)-1,3-butanedione (Compound 23)

mp.: 154°–155° C. (recrystallized from benzene-n-hexane).

IR $\nu_{max}^{KBr}$ cm$^{-1}$: 3080, 1560, 1350, 1330, 1285.

NMR (CDCl$_3$) δ: 7.5 (1H, d), 7.3 (2H, s), 7.1 (1H, d) 6.5 (1H, q), 2.1 (3H, s).

EXAMPLE 24

2-(1,3-dithiol-2-ylidene)-1-(2-thienyl)-1,3-butanedione (Compound 24)

mp.: 110°–111° C. (recrystallized from benzene-n-hexane).

IR $\nu_{max}^{KBr}$ cm$^{-1}$: 3050, 1600, 1545, 1415, 1360, 1330, 1270.

NMR (CDCl$_3$) δ: 7.6 (1H, d.d), 7.4 (1H, d.d), 7.15 (2H, s) 7.1 (1H, m), 2.1 (3H, s).

EXAMPLE 25

2-(1,3-dithiol-2-ylidene)-1-(2-pyrrolyl)-1,3-butanedione (Compound 25)

mp.: 112°–114° C. (recrystallized from benzene-n-hexane).

IR $\nu_{max}^{KBr}$ cm$^{-1}$: 3000, 1605, 1550, 1403, 1363, 1320.

NMR (CDCl$_3$) δ: 6.9 (2H, s), 6.1–7.1 (4H, m), 2.2 (3H, s).

EXAMPLE 26

2-(1,3-dithiol-2-ylidene)-1-pyrazinyl-1,3-butanedione (Compound 26)

mp.: 181°–182° C. (recrystallized from ethyl acetate-benzene).

IR $\nu_{max}^{KBr}$ cm$^{-1}$: 3050, 1620, 1590, 1570, 1360, 1020.

NMR (CDCl$_3$) δ: 9.0 (1H, s), 8.6 (2H, m), 7.6 (2H, s), 1.85 (3H, s).

EXAMPLE 27

2-(1,3-dithiol-2-ylidene)-1-(1-naphthyl)-1,3-butanedione (Compound 27)

mp.: 158°–159° C. (recrystallized from benzene-n-hexane).

IR $\nu_{max}^{KBr}$ cm$^{-1}$: 3030, 1600, 1555, 1420, 1340, 1268, 790.

NMR (CDCl$_3$) δ: 7.7–8.15 (4H, m), 7.35–7.65 (3H, m), 7.4 (2H, s), 1.65 (3H, s).

EXAMPLE 28

2-(1,3-dithiol-2-ylidene)-1-(2-naphthyl)-1,3-butanedione (Compound 28)

mp.: 154°–155° C. (recrystallized from benzene-n-hexane).

IR $\nu_{max}^{KBr}$ cm$^{-1}$: 3050, 1560, 1430, 1310, 1300, 880, 740.

NMR (CDCl$_3$) δ: 8.05 (1H, br.s), 7.2–8.0 (6H, m), 7.25 (2H, s), 1.9 (3H, s).

EXAMPLE 29

2-(1,3-dithiol-2-ylidene)-1-(2-indolyl)-1,2-butanedione (Compound 29)

mp.: 98°–99° C. (recrystallized from benzene-n-hexane).

IR $\nu_{max}^{KBr}$ cm$^{-1}$: 3050, 1645, 1575, 1450, 1380, 1200.

NMR (CDCl$_3$) δ: 7.2–7.6 (5H, m), 7.0 (2H, s), 6.5 (1H, br.s), 2.1 (3H, s).

EXAMPLE 30

2-(1,3-dithiol-2-ylidene)-1-(2-quinolyl)-1,3-butanedione (Compound 30)

mp.: 197°–198° C. (recrystallized from benzene-n-hexane).

IR $\nu_{max}^{KBr}$ cm$^{-1}$: 3050, 1570, 1435, 1365, 1320, 1270, 850.

NMR (CDCl$_3$) δ: 8.3 (1H, d), 7.45–8.2 (5H, m), 7.3 (2H, s) 1.85 (3H, s).

EXAMPLE 31

2-(1,3-dithiol-2-ylidene)-1-phenyl-4,4,4-trifluoro-1,3-butanedione (Compound 31)

mp.: 77°–79° C. (recrystallized from aqueous methanol).

IR $\nu_{max}^{KBr}$ cm$^{-1}$: 3050, 1590, 1560, 1450, 1430, 1230.

NMR (CDCl$_3$) δ: 7.9 (2H, d.d), 7.4 (3H, m), 6.75 (2H, s).

EXAMPLE 32

3-(1,3-dithiol-2-ylidene)-1-phenyl-2,4-pentanedione (Compound 32)

mp.: 157.5°–158° C. (recrystallized from ethanol-acetone).

IR $\nu_{max}^{KBr}$ cm$^{-1}$: 3000, 1570, 1440, 1380, 1320, 1260.

NMR (d$_6$-DMSO) δ: 7.65 (2H, s), 7.15 (5H, s), 4.25 (2H, s), 2.6 (3H, s).

EXAMPLE 33

4-(1,3-dithiol-2-ylidene)-1-phenyl-1-hexene-3,5-dione (Compound 33)

mp.: 150° C. (recrystallized from benzene-n-hexane).
IR $v_{max}^{KBr}$ cm$^{-1}$: 3050, 1640, 1600, 1540, 1370, 1250, 1195.
NMR (CDCl$_3$) δ: 7.7 (1H, d), 7.1–7.7 (5H, m), 7.3 (2H, s), 7.2 (1H, d), 2.55 (3H, s).

EXAMPLE 34

2-(1,3-dithiol-2-ylidene)-1,3-diphenyl-1,3-propanedione (Compound 34)

mp.: 155°–156° C. (recrystallized from methanol).
IR $v_{max}^{KBr}$ cm$^{-1}$: 3080, 1588, 1560, 1360, 1271.
NMR (CDCl$_3$) δ: 7.3 (2H, s), 6.85–7.50 (10H, m).

EXAMPLE 35

2-(1,3-dithiol-2-ylidene)-1,3-di(4-chlorophenyl)-1,3-propanedione (Compound 35)

mp.: 147°–148° C. (recrystallized from methanol).
IR $v_{max}^{KBr}$ cm$^{-1}$: 3070, 1590, 1567, 1362, 1275.
NMR (CDCl$_3$) δ: 7.75 (4H, d), 7.3 (2H, s), 7.2 (4H, d).

EXAMPLE 36

2-(1,3-dithiol-2-ylidene)-1,3-di(4-methoxyphenyl)-1,3-propanedione (Compound 36)

mp.: 143° C. (recrystallized from ethyl acetate-benzene).
IR $v_{max}^{KBr}$ cm$^{-1}$: 3060, 1585, 1565, 1360, 1270.
NMR (CDCl$_3$) δ: 7.55 (4H, d), 7.1 (2H, s), 6.9 (4H, d), 3.6 (6H, s).

EXAMPLE 37

2-(1,3-dithiol-2-ylidene)-1,4-diphenyl-1,3-butanedione (Compound 37)

mp.: 116° C. (recrystallized from ethyl acetate-benzene).
IR $v_{max}^{KBr}$ cm$^{-1}$: 3040, 1595, 1585, 1360, 1270, 1000.
NMR (CDCl$_3$) δ: 7.8–6.8 (10H, m), 7.2 (2H, s), 3.6 (2H, s).

EXAMPLE 38

4-(1,3-dithiol-2-ylidene)-1,5-diphenyl-1-pentene-3,5-dione (Compound 38)

mp.: 174° C. (recrystallized from benzene-n-hexane).
IR $v_{max}^{KBr}$ cm$^{-1}$: 3030, 1640, 1600, 1550, 1380, 1290, 1000.
NMR (CDCl$_3$) δ: 7.3 (2H, s), 6.8–7.9 (11H, m), 6.4 (1H, d).

EXAMPLE 39

4-(1,3-dithiol-2-ylidene)-1,7-diphenyl-1,6-heptadiene-3,5-dione (Compound 39)

mp.: 218° C. (recrystallized from benzene).
IR $v_{max}^{KBr}$ cm$^{-1}$: 3050, 1630, 1570, 1360, 1240, 1060, 980.
NMR (CDCl$_3$) δ: 7.74 (2H, d), 7.35 (2H, s), 7.1–7.6 (12H, m).

EXAMPLE 40

2-(1,3-dithiol-2-ylidene)-1,3-cyclopentanedione (Compound 40)

mp.: 205°–207° C. (recrystallized from acetone-n-hexane).
IR $v_{max}^{KBr}$ cm$^{-1}$: 2920, 1610, 1430, 1410, 1300, 1250.
NMR (CDCl$_3$) δ: 7.9 (2H, s), 2.7 (4H, s).

EXAMPLE 41

2-(1,3-dithiol-2-ylidene)-1,3-cyclohexanedione (Compound 41)

mp.: 225°–226° C. (recrystallized from benzene.
IR $v_{max}^{KBr}$ cm$^{-1}$: 3100, 1590, 1380, 1262, 1190.
NMR (CDCl$_3$) δ: 7.4 (2H, s), 2.7 (4H, t), 2.0 (2H, t).

EXAMPLE 42

2-(1,3-dithiol-2-ylidene)-4-methyl-1,3-cyclohexanedione (Compound 42)

mp.: 147°–148° C. (recrystallized from acetone.
IR $v_{max}^{KBr}$ cm$^{-1}$: 3050, 1590, 1380, 1270, 1225, 720.
NMR (CDCl$_3$) δ: 7.45 (2H, s), 1.7–2.9 (5H, m), 1.3 (3H, d).

EXAMPLE 43

2-(1,3-dithiol-2-ylidene)-4-isopropyl-1,3-cyclohexanedione (Compound 43)

mp.: 115°–117° C. (recrystallized from ethyl acetate-ether).
IR $v_{max}^{KBr}$ cm$^{-1}$: 2950, 1592, 1380, 1278, 1275, 700.
NMR (CDCl$_3$) δ: 7.45 (2H, s), 1.7–3.0 (6H, m), 1.2 (3H, d).

EXAMPLE 44

2-(1,3-dithiol-2-ylidene)-5,5-dimethyl-1,3-cyclohexanedione (Compound 44)

mp.: 201° C. (recrystallized from benzene-n-hexane).
IR $v_{max}^{KBr}$ cm$^{-1}$: 2950, 1585, 1380, 1338, 1280, 715.
NMR (CDCl$_3$) δ: 7.45 (2H, s), 2.5 (4H, s), 1.1 (6H, s).

EXAMPLE 45

To 50 ml of dry tetrahydrofuran, 0.7 g of 50% oil-based sodium hydride was suspended, and 2.2 g of 1-(4-methoxymethyloxyphenyl)-1,3-butanedione was gradually added under cooling with ice. After the completion of the generation of hydrogen gas, 3.3 g of 2-methylthio-1,3-dithiolylium perchlorate was added thereto, and the mixture was stirred for 1 hour. Then, the solvent was removed from the reaction solution by distillation under reduced pressure.

Ice water was added to the residue, and then the desired product was extracted with chloroform. The chloroform extract was concentrated under reduced pressure, and the residue was purified by silicagel chromatography, whereby 2.7 g of 2-(1,3-dithiol-2-ylidene)-1-(4-methoxymethyloxyphenyl)-1,3-butanedione was obtained. The above product was dissolved in 50 ml of isopropyl alcohol containing 0.7% (W/W) hydrogen chloride, and the solution was aged for 30 minutes at 60° C. Then, the solvent was evaporated under reduced pressure, and the residue was recrystallized from benzene-n-hexane, whereby 2.5 g (yield: 66%) of 2-(1,3-dithiol-2-ylidene)-1-(4-hydroxyphenyl)-1,3-butanedione was obtained as crystals having a melting point of from 74° to 76° C.

IR $\nu_{max}^{KBr}$ cm$^{-1}$: 3105, 1620, 1590, 1280, 1220, 1165, 1000.

NMR (CDCl$_3$) δ: 9.1 (1H, s), 7.3 (2H, d), 7.2 (2H, s) 6.75 (2H, d), 2.1 (3H, s).

EXAMPLE 46

Two and six-tenth gram of 2-(1,3-dithiol-2-ylidene)-1-(4-t-butoxy-carbonylaminophenyl)-1,3-butanedione, obtained in the same manner as in Example 1 using 2.8 g of 1-(4-t-butoxy-carbonylaminophenyl)-1,3-butanedione and 2.8 g of 2-methylthio-1,3-dithiolylium perchlorate, was dissolved in 5 ml of trifluoroacetic acid. Then, the solution was aged for 3 hours at room temperature, and to its solution, 50 ml of n-hexane was added under stirring.

The product was filtered and recrystallized from ethyl acetate, whereby 1.7 g (yield: 89%) of 2-(1,3-dithiol-2-ylidene)-1-(4-aminophenyl)-1,3-butanedione was obtained as crystals having a melting point of from 168° to 169° C.

IR $\nu_{max}^{KBr}$ cm$^{-1}$: 3350, 1600, 1540, 1390, 1260.

NMR (CDCl$_3$) δ: 7.45 (2H, d), 7.1 (2H, s), 6.6 (2H, d) 5.0 (2H, s), 2.0 (3H, s).

EXAMPLE 47

By using 2.0 g of 1-(2-benzimidazolyl)-1,3-butanedione and 2.5 g of 2-methylthio-1,3-dithiolylium perchlorate, the treatment was conducted in the same manner as in Example 1. The product was purified by silicagel chromatography, whereby 0.87 g (yield: 29%) of 2-(1,3-dithiol-2-ylidene)-1-(2-benzimidazolyl)-1,3-butanedione was obtained as crystals having a decomposition point of 254° C.

IR $\nu_{max}^{KBr}$ cm$^{-1}$: 1615, 1565, 1427, 1335, 760, 700.

NMR (CDCl$_3$) δ: 7.7 (2H, s), 7.1–7.7 (4H, m), 2.0 (3H, s).

Pharmacological Test

1. Protective Effect on Acute Liver Injury Induced by Carbon Tetrachloride

A test compound was dissolved or suspended in olive oil and administered orally at a dose of 50 mg/kg to mice (ddY, mice, ♂, 23±2 g, n=5). After 6 hours, carbon tetrachloride (0.05 ml/kg) was administered orally, 24 Hours after the administration of carbon tetrachloride, BSP (sodium sulfobromophthalene; 75 mg/kg) was administered intravenously. Thirty minutes later, the cardiac blood was collected, and GPT (glutamic-pyruvic transaminase) activity and the retention rate of BSP in the plasma were measured. Further, the liver injury immediately after the collection of the blood was visually observed and evaluated by the following score for liver damage index.

0: normal
2: Slightly injured
4: distinctly injured
6: remarkably injured

As shown in Table 1, the test compounds showed substantial effects for preventing the liver injury with respect to each of the test items.

TABLE 1

| Compound No. | Liver Damage Index | % Prophylaxis p-GPT | BSP |
|---|---|---|---|
| 1 | 5.0 | 25 | 80 |
| 2 | 1.4 | 72 | 85 |
| 3 | 2.2 | 97 | 102 |
| 4 | 1.0 | 100 | 108 |
| 5 | 2.8 | 89 | 96 |
| 6 | 0.4 | 100 | 103 |
| 7 | 1.6 | 100 | 108 |
| 8 | 1.2 | 100 | 110 |
| 9 | 0.4 | 100 | 103 |
| 10 | 2.0 | 42 | 78 |
| 11 | 0.8 | 100 | 105 |
| 12 | 0.6 | 100 | 114 |
| 14 | 0.4 | 100 | 113 |
| 15 | 3.2 | 100 | 105 |
| 16 | 0.6 | 99 | 95 |
| 17 | 0 | 100 | 100 |
| 18 | 0.4 | 54 | 100 |
| 19 | 1.6 | 100 | 100 |
| 21 | 0.8 | 98 | 100 |
| 22 | 0.2 | 100 | 120 |
| 23 | 1.0 | 94 | 110 |
| 24 | 0 | 100 | 102 |
| 25 | 2.2 | 76 | 88 |
| 26 | 0.4 | 96 | 99 |
| 27 | 0 | 100 | 100 |
| 28 | 0 | 99 | 100 |
| 29 | 0.8 | 100 | 104 |
| 30 | 2.0 | 98 | 105 |
| 31 | 0.4 | 100 | 106 |
| 32 | 0.4 | 95 | 124 |
| 33 | 4.2 | 77 | 86 |
| 34 | 0.8 | 100 | 112 |
| 35 | 0 | 100 | 114 |
| 36 | 0 | 100 | 119 |
| 37 | 1.8 | 100 | 99 |
| 38 | 3.2 | 66 | 96 |
| 41 | 6.0 | 29 | 66 |
| 42 | 6.0 | 29 | 60 |
| 43 | 5.6 | 67 | 95 |
| 44 | 1.2 | 95 | 111 |
| 45 | 0.2 | 100 | 111 |
| 46 | 0.4 | 100 | 106 |
| 47 | 2.4 | 91 | 103 |
| CCl$_4$ alone | 6.0 | 0 (4413 ± 455)* | 0 (57 ± 8)* |
| Normal | 0 | 100 (18 ± 2)* | 100 (15 ± 1)* |

*The value in parentheses represents mean ± S.E.

2. Therapeutic Effect on Fatty Liver Induced by Carbon Tetrachloride

Carbon tetrachloride (1 ml/kg) was subcutaneously administered to rats (SD strain, ♂, 38 week-old, n=5) for 4 days. Upon expiration of 3 days from the administration of carbon tetrachloride, Compound 6 was orally given successively for 7 days at the dose of 50 mg/kg. On the 8th day, the animals were sacrificed by exsanguination. The therapeutic effect was evaluated by examining the content of triglyceride in the liver and the concentration of apoprotein B in the plasma. As shown in Table 2, Compound 6 exhibited a significant effect for curing the fatty liver.

TABLE 2

| | Triglyceride (mg/g-liver) | Apoprotein (mg/ml-plasma) |
|---|---|---|
| Compound 6 | 33 ± 7 | 112 ± 23 |
| CCl$_4$ alone | 99 ± 6 | 66 ± 2 |
| Normal | 33 ± 5 | 125 ± 8 |

3. Protective Effect on Acute Liver Injury Induced by D-Galactosamine

A test compound was dissolved or suspended in olive oil and orally administered twice daily for 6 days at a dose of 50 mg/kg to rats (SD strain, ♂, 225±15 g, 7 weeks-old, n=5). On the 6th day, D-galactosamine (200 mg/kg×3) was intraperitoneally administered three times at 3-hour intervals. 48 Hours after the first injection of D-galactosamine, the animals were sacrificed by exsanguination from the abdominal aorta. The protective effect was evaluated by examining the biochemical parameters (p-GPT, glucose, alkaline phosphatase) in plasma.

As shown in Table 3, the test compounds showed substantial effects for preventing the liver injury.

TABLE 3

| Test Compound | P—GPT (U/l) | Glucose (mg/dl) | ALP (U/l) |
|---|---|---|---|
| Compound 6 | 908 ± 248 | 81 ± 9 | 398 ± 45 |
| Compound 47 | 2938 ± 694 | 55 ± 2 | 287 ± 25 |
| D-Galactosamine alone | 4825 ± 590 | 32 ± 4 | 176 ± 6 |
| Normal | 29 ± 2 | 142 ± 4 | 500 ± 63 |

4. Effect on Protein Synthesis in Liver

Compound 6 was dissolved in olive oil and orally administered successively for 3 days at a dose of 100 mg/kg to rats (Wister strain, ♂, 180±10 g, 6 week-old, n=5). 24 Hours after the administration of the test compound was completed, the animals were sacrificed. The effect on the protein synthesis in the liver was evaluated by determining the liver weight and protein content.

As shown in Table 4, Compound 6 showed substantial effect for stimulating the protein metabolic function of the liver.

TABLE 4

| | Liver Weight (g/100 g b.w.) | Liver Protein (mg/100 g b.w.) |
|---|---|---|
| Control | 6.3 ± 0.1 | 883 ± 79 |
| Compound 6 | 8.6 ± 0.3 | 1247 ± 62 |

5. Acute Toxicity Test

A test compound was dissolved or suspended in olive oil and administered orally to mice (ddY mice, ♂, 23±2 g, n=5). The acute toxicity value (LD$_{50}$) was determined from the mortality one week after the administration.

The test compounds (Compound Nos. 4, 5, 6, 7, 8, 12, 17, 27, 28 and 45) showed low toxicity and their LD$_{50}$ values were at least 2 g.

We claim:

1. A 1,3-dithiol-2-ylidene derivative of the formula:

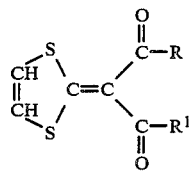

(I)

wherein each of R and R$^1$ may be the same or different, and is selected from the group consisting of a C$_{1-6}$ alkyl group, a C$_{2-4}$ alkenyl group, a C$_{3-6}$ cycloalkyl group, a C$_{1-3}$ alkoxy-C$_{1-4}$-alkyl group, phenyl, naphthyl, benzyl, naphthylmethyl, furyl, thienyl, pyrrolyl, imidazolyl, pyridyl, pyazinyl, indolyl, quinolyl, and benzimidazolyl group, which may be substituted by halogen, hydroxyl, lower alkyl, lower alkoxy, nitro, cyano, or lower alkoxycarbonyl or R and R$^1$ together form an ethylene or trimethylene group which may be substituted by C$_{1-4}$ alkyl, benzyl, naphthyl, methyl, phenyl, or naphthyl.

2. The derivative according to the claim 1, wherein each of R and R$^1$ is methyl, ethyl, propyl, isopropyl, butyl, isobutyl, tert-butyl, pentyl, hexyl, vinyl, 2-methylvinyl, cyclopentyl, cyclohexyl, ethoxymethyl, 2-methoxyethyl, 3-ethoxypropyl, 3-propoxypropyl, 2-ethoxybutyl, or a phenyl, naphthyl, benzyl, naphthylmethyl, furyl, thienyl, pyrrolyl, imidazolyl, pyridyl, pyrazinyl, indolyl, quinolyl or benzimidazolyl group which may be substituted by halogen, hydroxyl, lower alkyl, lower alkoxy, nitro, cyano or lower alkoxycarbonyl, or R and R$^1$ together form an ethylene or trimethylene group which may be substituted by lower alkyl, benzyl, naphthylmethyl, phenyl or naphthyl.

3. A compound according to claim 1, which is selected from the group consisting of
3-(1,3-dithiol-2-ylidene)-2,4-pentanedione, 3-(1,3-dithiol-2-ylidene)-2,4-hexanedione, 3-(1,3-dithiol-2-ylidene)-1-ethoxy-2,4-pentanedione, 5-(1,3-dithiol-2-ylidene)-2,8-dimethyl-4,6-nonanedione, 2-(1,3-dithiol-2-ylidene)-1-cyclohexyl-1,3-butane-dione, 3-dithiol-2-ylidene)-1-phenyl-1,3-butanedione, 2-(1,3-dithiol-2-ylidene)-1-phenyl-,1,3-hexanedione, 2-(1,3-dithiol-2-ylidene)-5-methyl-1-phenyl-1,3-hexanedione, 2-(1,3-dithiol-2-ylidene)-4,4-dimethyl-1-phenyl-1,3-pentanedione,
2-(1,3-dithiol-2-ylidene)-1-phenyl-1,3-octadecanedione,
2-1,3-dithiol-2-ylidene)-1-phenyl-4-hexene-1,3-dione,
2-(1,3-dithiol-2-ylidene)-1-(4-methylphenyl)-1,3-butanedione,
2-(1,3-dithiol-2-ylidene)-1-(4-fluorophenyl)-1,3-butanedione,
2-(1,3-dithiol-2-ylidene)-1-(4-chlorophenyl)-1,3-butanedione,
2-(1,3-dithiol-2-ylidene)-1-(4-bromophenyl)-1,3-butanedione,
2-(1,3-dithiol-2-ylidene)-1-(2-methoxyphenyl)-1,3-butanedione,
2-(1,3-dithiol-2-ylidene)-1-(4-methoxyphenyl)-1,3-butanedione,
2-(1,3-dithiol-2-ylidene)-1-(3,4-dimethoxyphenyl)-1,3-butanedione,
2-(1,3-dithiol-2-ylidene)-1-(4-nitrophenyl)-1,3-butanedione,
2-(1,3-dithiol-2-ylidene)-1-(2-pyridyl)-1,3-butanedione,
2-(1,3-dithiol-2-ylidene)-1-(3-pyridyl)-1,3-butanedione,
2-(1,3-dithiol-2-ylidene)-1-(4-pyridyl)-1,3-butanedione,
2-(1,3-dithiol-2-ylidene)-1-(2-furyl)-1,3-butanedione,
2(1,3-dithiol-2-ylidene)-1-(2-thienyl)-1,3-butanedione,
2-(1,3-dithiol-2-ylidene)-1-(2-pyrrolyl)-1,3-butanedione,
2-(1,3-dithiol-2-ylidene)-1-pyrazinyl-1,3-butanedione,
2-(1,3-dithiol-2-ylidene)-1-(1-naphthyl)-1,3-butanedione,
2-(1,3-dithiol-2-ylidene)-1-(2-naphthyl)-1,3-butanedione,
2-(1,3-dithiol-2-ylidene)-1-(2-indolyl)-1,3-butanedione,
2-(1,3-dithiol-2-yidene)-1-(2-quinolyl)-1,3-butanedione,
2-(1,3-dithiol-2-ylidene)-1-phenyl-4,4,4-trifluoro-1,3-butanedione,
3-(1,3-dithiol-2-ylidene)-1-phenyl-2,4-pentanedione,
4-(1,3-dithiol-2-ylidene)-1-phenyl-1-hexene-3,5-dione,
2-(1,3-dithiol-2-ylidene)-1,3-diphenyl-1,3-propanedione,
2-(1,3-dithiol-2-ylidene)-1,3-di(4-chloro-phenyl)-1,3-propanedione,
2-(1,3-dithiol-2-ylidene)-1,3-di(4-methoxy-phenyl)-1,3-propanedione, 2-(1,3-dithiol-2-ylidene)-1,4-diphenyl-1,3-butanedione,
4-(1,3-dithiol-2-ylidene)-1,5-diphenyl-1-pentene-3,5-dione,
4l -(1,3-dithiol-2-ylidene)-1,7-diphenyl-1,6-heptadiene-3,5-dione,
2-(1,3-dithiol-2-ylidene)-1,3-cyclopentane-dione,
2-(1,3-dithiol-2-ylidene)-1,3-cyclohexane-dione,
2-(1,3-dithiol-2-ylidene)-4-methyl-1,3-cyclohexanedione,
2-(1,3-dithiol-2-ylidene)-4-(2-methylethyl)-1,3-cyclohexanedione,
2-(1,3-dithiol-2-ylidene)-5,5-dimethyl-1,3-cyclohexanedione,
3-(1,3-dithiol-2-ylidene)-1-(4-hydroxylphenyl)-1,3-butanedione,
2-(1,3,-dithiol-2-ylidene)-1-(4-aminophenyl)-1,3-butanedione, or
2-(1,3-dithiol-2-ylidene)-1-(2-benzimidazolyl)-1,3-butanedione.

4. A pharmaceutical composition for treating hepatitis or cirrhotic liver disease, which comprises a liver-disease treating effective amount of a 1,3-dithiol-2-ylidene derivative of the formula I as defined in claim 1 and a pharmaceutically acceptable carrier or diluent.

5. A pharmaceutical composition according to claim 4, wherein said composition is for oral administration, and delivers from 0.1 to 25 milligrams of said 1,3-dithiol-2-ylidene derivative per day per kilogram body weight.

6. The pharmaceutical composition according to claim 4, wherein said composition is for parenteral administration, and delivers from 0.1 to 10.0 milligrams of said 1,3-dithiol-2-ylidene derivative per day per kilogram body weight.

* * * * *